(12) United States Patent
Fischer et al.

(10) Patent No.: US 7,518,373 B2
(45) Date of Patent: Apr. 14, 2009

(54) MAGNETIC RESONANCE SYSTEM WITH RECEPTION ANTENNA DEVICE

(75) Inventors: Hubertus Fischer, Bamberg (DE); Martin Hergt, Chatelaine (CH); Thomas Kundner, Buckenhof (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/924,777

(22) Filed: Oct. 26, 2007

(65) Prior Publication Data

US 2008/0106264 A1    May 8, 2008

(30) Foreign Application Priority Data

Nov. 6, 2006  (DE) ............... 10 2006 052 217

(51) Int. Cl.
*G01V 3/00*  (2006.01)
(52) U.S. Cl. .................................... 324/322
(58) Field of Classification Search ......... 324/300–322; 600/410–435; 333/219–235; 343/729, 739–744, 343/850–872
See application file for complete search history.

(56) References Cited

U.S. PATENT DOCUMENTS

| | | | |
|---|---|---|---|
| 4,680,549 A | 7/1987 | Tanttu | |
| 5,201,312 A | 4/1993 | Schenck et al. | |
| 5,664,568 A | 9/1997 | Srinivasan et al. | |
| 2003/0016017 A1 | 1/2003 | Reykowski et al. | |
| 2005/0122113 A1 | 6/2005 | Okamoto et al. | |
| 2005/0242812 A1 | 11/2005 | Okamoto et al. | |
| 2008/0197849 A1* | 8/2008 | Heid et al. | 324/318 |

FOREIGN PATENT DOCUMENTS

| | | |
|---|---|---|
| DE | 10 2005 056 711 | 5/2007 |
| WO | WO 2005/050237 | 6/2005 |

* cited by examiner

*Primary Examiner*—Dixomara Vargas
(74) *Attorney, Agent, or Firm*—Schiff Hardin LLP

(57) ABSTRACT

A magnetic resonance system that has a magnet system that generates magnetic fields in an excitation region, allowing nuclei in an examination subject in the excitation region to be excited to emit a magnetic resonance signal. A reception antenna device with multiple local coils for reception of the magnetic resonance signals is arranged in proximity to the examination subject, and has a base part and an attachment part. The attachment part can be placed on the base part such that the examination subject is located between the base part and the attachment part (6). The multiple local coils are respectively connected with an evaluation device for evaluation of magnetic resonance signals. To simply and reliably couple the antenna devices to an evaluation device with optimally few electrical conductors being located in the excitation region, the multiple local coils in the attachment part are respectively connected with the evaluation device via a base coupling element that is arranged at a predetermined base part location on the base part and an attachment coupling element is arranged at a predetermined attachment part location on the attachment part. The magnetic resonance signal received by the local coil can be fed to the evaluation device via the attachment coupling element and the base coupling element and as long as the attachment part is placed on the base part.

11 Claims, 4 Drawing Sheets

MAGNETIC RESONANCE SYSTEM WITH RECEPTION ANTENNA DEVICE

BACKGROUND OF THE INVENTION

1. Field of the Invention

The present invention concerns a magnetic resonance system of the type having a magnet system that generates a magnetic field in an excitation region, allowing nuclei in an examination subject in the excitation region to be excited to emit a magnetic resonance signal, and a reception antenna device with a number of local coils for reception of the magnetic resonance signal, in proximity to the examination subject, and that has a base part and an attachment part; the attachment part being attached to the based part such that the examination subject is located between the base part and the attachment part; with the local coils being respectively connected with an evaluation device for evaluation of magnetic resonance signals.

2. Description of the Prior and Related Subject Matter

Magnetic resonance systems of the above type are generally known.

Conventionally, the acquisition of magnetic resonance signals emitted from the examination subject ensues either with a whole-body antenna or with local coils. If the magnetic resonance signal is acquired with a whole-body antenna, the magnetic resonance signal can be acquired from the entire excitation region. The acquisition, however, may occur only with relatively low signal-to-noise ratio (SNR). Therefore local coils are also used in many cases in magnetic resonance systems, often multiple local coils. The local coils are arranged near to the examination subject (normally a person) and can therefore receive signals with a good SNR, although only from a small part of the excitation region. Moreover, spatial coding by gradient fields can be supplemented due to spatial resonance by the arrangement of the local coils as such. The required measurement time for an acquisition thus can also be reduced.

In conventional magnetic resonance systems, all local coils are connected by a corresponding number of connectors (attached to the patient bed) and a movable cable harness to an evaluation device that is arranged on the base body. Due to the attenuation of the long, thin cables employed, preamplifiers must be arranged in the local coils. Furthermore, each local coil must have a detuning circuit that deactivates the coil given non-use and upon transmission. Elaborate common mode chokes (known as sheath wave barriers) must also be inserted into the long cable harness in order to be able to limit induced voltages during transmission.

A plug connection for local coils that operates without contact (namely via inductive coupling) is known from DE 101 30 615 C2. This teaching represents an advance since a galvanic contact between the local coil and the evaluation device is no longer necessary for coupling of a local coil to the evaluation device. As is conventional, however, the necessity exists of actively plugging the connection by operating personnel. The local coil must also be specifically connected to the evaluation device or disconnected from it.

From DE 35 00 456 C2 it is known to couple a local coil with the whole-body antenna. A contact-free coupling is achieved, but this coupling is possible only for a single local coil, and even then only given suitable orientation of the local coil. Moreover, the teaching of DE 35 00 456 C2 can not be extended to multiple local coils. Here as well the local coil must also be actively connected to the whole-body antenna or disconnected from it.

From EP 0 437 049 A2 it is known to directly, inductively couple a local coil to another coil that is arranged in immediate proximity of the local coil. For this purpose the local coil must also be actively connected to the evaluation device or disconnected from it.

An approach to overcome the mechanical plug connection between the electrical circuits of the moving part and the stationary base part of a magnetic resonance system is disclosed in DE 10 2005 056711 B3.

A wireless connection of local coils for an MR system is described therein. The coupling ensues either inductively or capacitively. The problem of making an electrical connection in the antenna devices that are intended for specific body parts, and that can be installed as needed in a magnetic resonance system, is not solved by this proposal. For example, for an antenna device adapted to the head shape for examinations of the head of a patient in a magnetic resonance system, the local coils are arranged closer to the tissue to be examined and thus ensure a stronger signal with better signal-to-noise ratio.

A radio-frequency device with coil that has a radio-frequency coil in order to receive a magnetic resonance signal and that has a second unit with a second radio-frequency coil with which the magnetic resonance signal is received independently of the first radio-frequency coil is known from US 2005/0242812 A1. The first and second units are supported by a carrier. The carrier can be detached from at least one of the first and second units. The carrier is configured such that the alignment of first unit in relation to the second unit can be changed.

SUMMARY OF THE INVENTION

An object of the present invention is to provide a magnetic resonance system of the aforementioned type but wherein the reception antenna devices with one or more local coils can be simply and reliably coupled to an evaluation device, with optimally few electrical conductors being located in the excitation region.

The above object is achieved in accordance with the present invention by a magnetic resonance system of the type initially described, wherein the multiple local coils are respectively connected to the evaluation device by a base coupling element disposed at a predetermined base part location on the base part, and an attachment coupling element that is arranged at a predetermined attachment part location on the attachment part, so that the magnetic resonance signal received by a local coil is fed to the evaluation device via the attachment coupling element and the base coupling element, as long as the attachment part is placed on the base part, and the magnetic resonance system further having a protective circuit between the base coupling element and the evaluation circuit. The protective circuit compensates the series resistance of the local coil and the attachment coupling element and the base coupling element, given feed of a magnetic resonance signal from the local coil to the evaluation circuit via the attachment coupling element and the base coupling element. The protective circuit furthermore detunes the base coupling element when no attachment coupling element is interacting with the base coupling element.

The base coupling element is advantageously connected with the evaluation device by a preamplifier.

In a further embodiment, the base coupling element is fashioned such that it detunes the local coil when the local coil cannot be coupled to the evaluation device.

In a further embodiment, the base coupling element and the attachment coupling element are inductive transfer devices.

In a further embodiment, a capacitive transformation circuit having a number of capacitors is arranged between the first base coupling element and the local coil.

In another embodiment, the base coupling element and the attachment coupling element are capacitive transfer devices.

In another embodiment, the attachment coupling element and the base coupling element are formed as a pair of narrow coupling strips.

In further embodiment, the coupling strips of the attachment coupling element are adjacent to one another on their longitudinal sides.

In an embodiment, a choke is connected in parallel with the attachment coupling element.

In a further embodiment, a protective element is arranged between the base coupling element and the evaluation circuit. The protective element compensates the series resistance of the local coil, the attachment coupling element, and the base coupling element upon feed of a magnetic resonance signal from the local coil via the attachment coupling element and the base coupling element to the evaluation circuit, and detunes the base coupling element when no attachment coupling element interacts with the base coupling element.

In another embodiment, the base coupling element can be detuned by a controllable blocking circuit.

In a further embodiment, a signal splitter is arranged between the base part body coupling element and the evaluation circuit, the signal path is connected with an RF driver element, and a magnetic resonance excitation signal emitted from the RF driver element can be fed via the base body coupling element and the attachment coupling element into the local coil, as long as the attachment part is attached.

DESCRIPTION OF THE PREFERRED EMBODIMENTS

Figure 1:
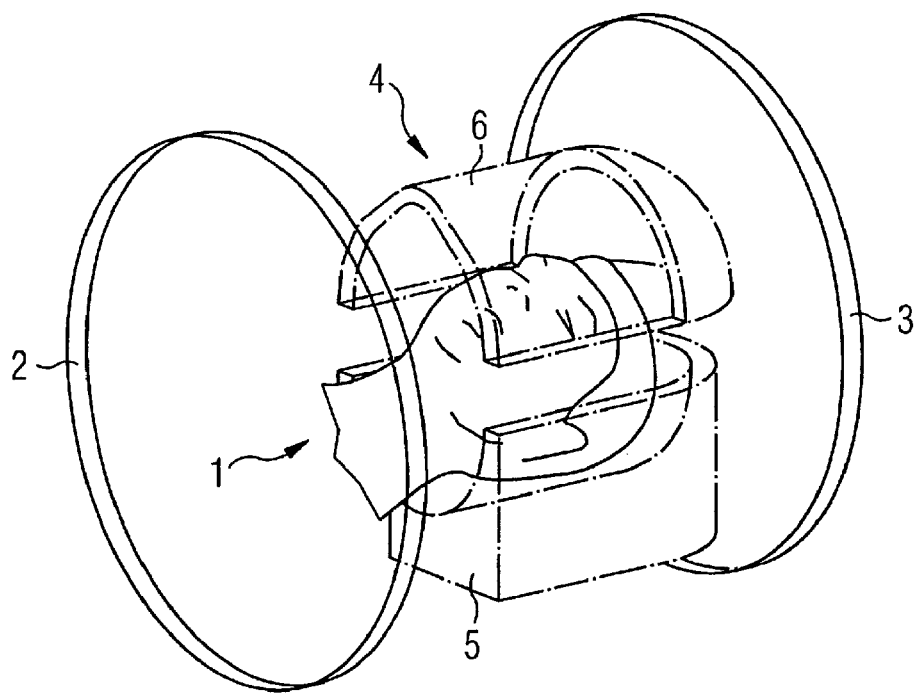
FIG. 1 schematically illustrates a magnetic resonance system for the head of a patient, in a perspective, partially transparent representation.

The drawings are not true to scale. Identical or identically-operating elements are provided with the same reference characters insofar as not otherwise mentioned.

FIG. 1 schematically shows, in perspective and partially-transparent representation, a magnetic resonance system in which a mobile antenna system is installed, with which a body part of a patient can be examined in a targeted manner. In FIG. 1 and in the following description it is assumed that the examination concerns the head of a patient, but it is understood by those skilled in the art that the following considerations can also be employed for other body parts such as, for example, the extremities.

The magnetic resonance system for examination of a patient 1 essentially has at least one pair of coils 2 and 3 for generation of a substantially homogeneous magnetic field (in which the patient 1 is located) at the examination location. Moreover, the magnet system can have gradient magnets (not shown) for generation of gradient fields for spatial coding, as well as further magnets.

A radio-frequency field is radiated into the examination subject 1 by a transmission antenna (not shown) in order to generate temporally spaced spin echoes in the subject 1.

It is possible to acquire the emitted magnetic resonance signal with a whole-body antenna (not shown) and to feed the acquired signal to an evaluation device with which the magnetic resonance signal can be evaluated. Only a qualitatively lower-grade reconstruction of the examination subject 1 is possible in this manner. Therefore, an antenna device 4 with local coils is used in the primary magnetic field generated by the coil pair 2, 3 (and possible further coils), the local coils being closer to the examination subject 1 in this manner. The antenna device 4 has a base part 5 and an attachment part 6. The base part 5 can be movable within the magnetic resonance system, and is fixed at a location in the system only for the examination itself. The attachment part 6 can be detached from the base part 5 so that the patient 1 inside can be placed comfortably and optimally, and is fixed on the base part 5 only for examination purposes.

Figure 2:
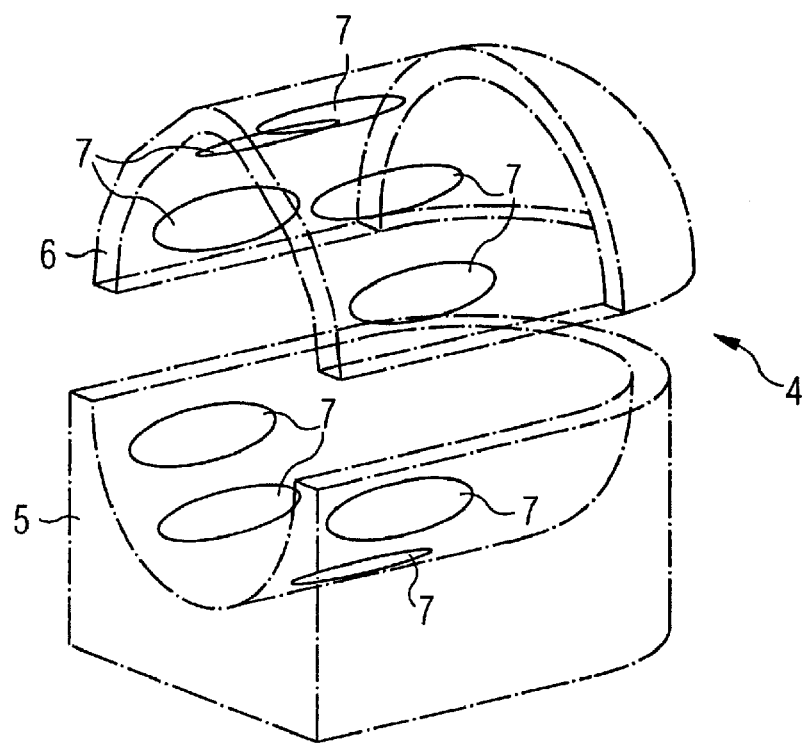
FIG. 2 shows the antenna device of FIG. 1, schematically in perspective representation.

In the following, details of the antenna device 4 are explained using FIG. 2. Both the base part 5 and the attachment part 6 of the antenna device 4 comprise a plurality of local coils 7. These are respectively distributed across the base part 5 or the attachment part 6 so that they come as close as possible to the examination subject. In FIG. 2 the local coils 7 are shown as ellipses. Four such coils 7 are shown in the base part 5 and five local coils 7 are shown distributed across the attachment part 6. The distribution of the local coils 7 over the antenna device 4 normally depends on its geometry. Overall, a significantly higher-grade magnetic resonance signal can be acquired via the local coils 7 in this manner, but only over a small volume per local coil 7.

In the prior art the local coils 7 are respectively connected with an evaluation device via a cable (not shown), in which evaluation device the signals acquired by the local coils 7 are analyzed and prepared for the presentation.

By contrast, according to the invention only some of the local coils 7 are directly connected with the evaluation device via a cable, while other local coils 7 are connected with the evaluation device via suitable transfer devices. The manner of the connection of the local coils 7 to the evaluation device is the subject matter of the present invention and is explained in the following using FIG. 3.

As can be seen from FIG. 2, a number of local coils 7 are normally arranged on the examination subject 1. Those local coils 7 that are located in a predominantly permanently-installed antenna device are connected with the analysis device via a cable connection. In the embodiment of the magnetic resonance system according to FIG. 3, the local coils 7 in the lower base part 5 are correspondingly connected with an evaluation device 9 via multiple-conductor cables 8, the individual conductors of the cable 8 being designated with 8a.

It is different in the attachment part 6 of the antenna device 4; the local coils 7 are not directly connected with the evaluation device 9 but rather are connected with their respectively separate transfer device, which enables a wireless transfer of the signals between the local coil 7 and the evaluation device 9. Each transfer device has an attachment coupling element 10 and a base coupling element 11. Each attachment coupling element 10 is connected with a local coil 7 via a separate individual line 12. Analogously, each base coupling element 11 is connected with the evaluation device 9 via a separate individual line 13. A number of individual lines 13 are directed to a specific point by the transfer cable 8.

The attachment coupling elements 10 are permanently connected with the attachment part 6. They are arranged at predetermined locations (not shown) of the attachment part 6. Insofar as it is necessary, these locations are subsequently called docking positions since they are determined with regard to their position relative to the base part 5.

The base coupling elements 11 are likewise located at predetermined locations (not shown) of the base part 5. These locations are arranged precisely opposite the aforementioned docking positions when the attachment part 6 is placed on the base part 5, such that a stable and reliable inductive or capacitive coupling is accomplished between the two coupling elements.

Figure 3:
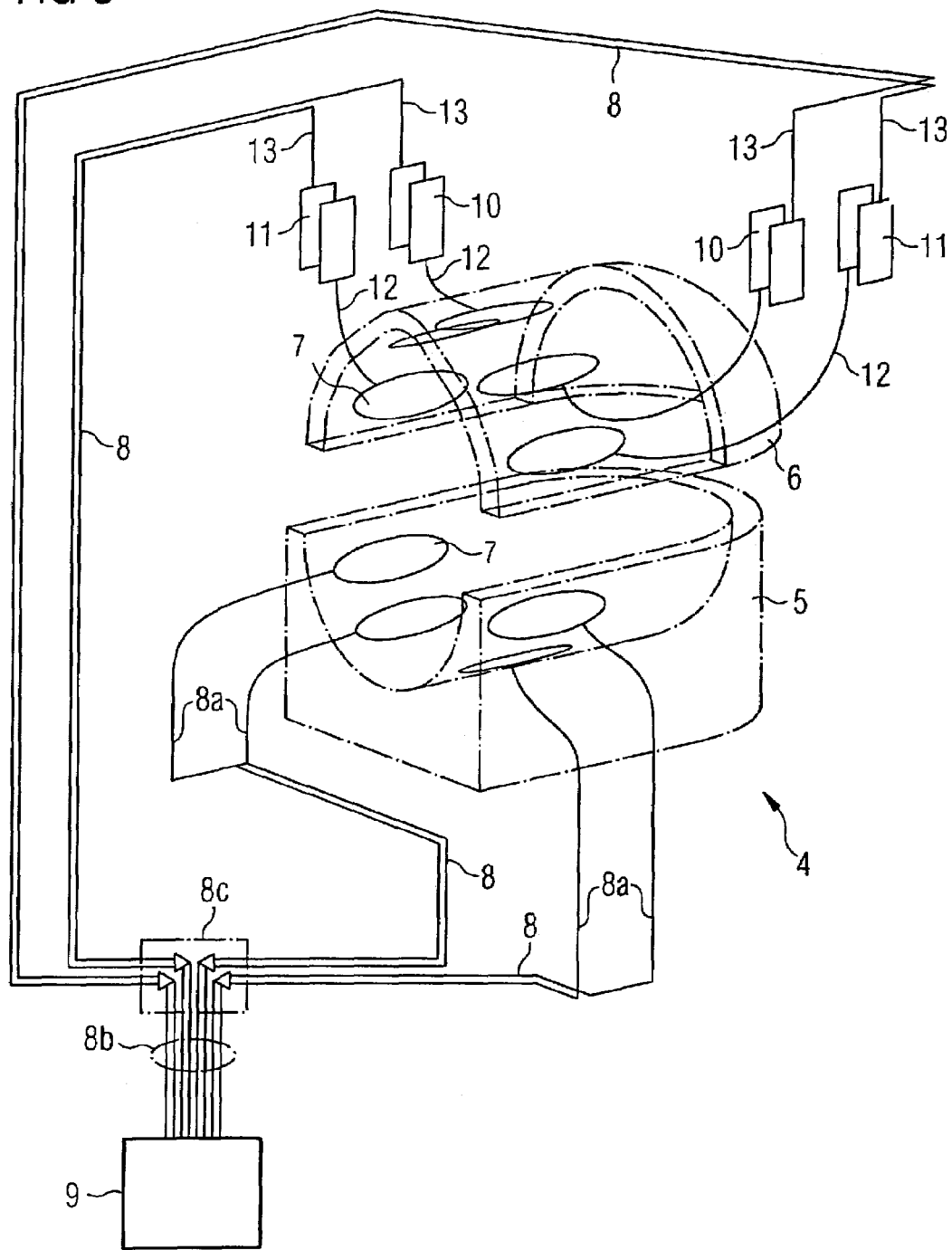
FIG. 3 schematically shows the electrical interconnection of the antenna device of FIGS. 1 and 2, FIG. 4 schematically illustrates possible arrangements of attachment coupling elements relative to base coupling elements.

In order to keep the number of free cables in the measurement volume as low as possible, the transfer cables 8 are merged into a plug device 8c at an advantageously situated location and from there are directed further as a single cable bundle 8b up to the actual evaluation device. The cable bundle 8b is indicated by a border surrounding the single cable 8. The plug device 8c (which is indicated in FIG. 3 by a dashed box) is advantageously located directly in the base part, such that in the ideal case only the cable bundle 8b from the reception antenna device 4 to the evaluation device 9 is located in the measurement volume. The effort of the medical personnel in the preparation of the measurement is therewith reduced to a minimum.

The transfer of the signals via the transfer devices with the respective coupling elements 10, 11 is explained in detail in the following in connection with FIG. 4.

Figure 4:
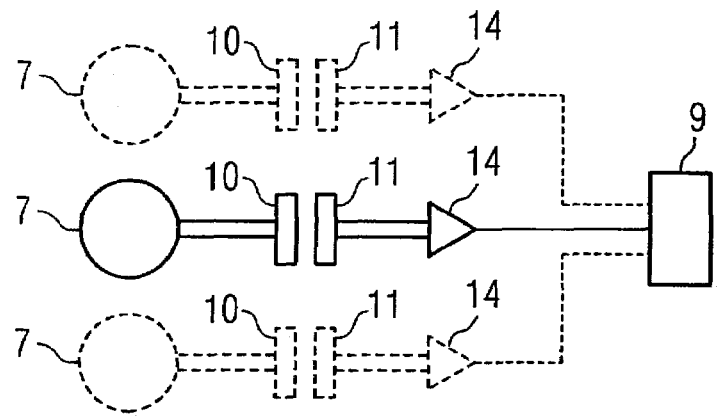

A transfer channel is represented in solid lines in FIG. 4. According to FIG. 4, a local coil 7 is thereby connected with an attachment coupling element 10. The attachment coupling element 10 couples with a base coupling element 11. The base coupling element 11 is connected via a preamplifier 14 with the evaluation device 9.

In all cases a plurality of such transfer channels exist at a specific point in time. This is shown dashed in FIG. 4 for two additional transfer channels. However, exclusively the transfer channel marked in solid lines is considered first in the following, the elements 7, 10, 11 of which transfer channel are subsequently designated as first elements 7, 10, 11, thus as a first local coil 7, first attachment coupling element 10 and first base coupling element 11.

Figure 5:
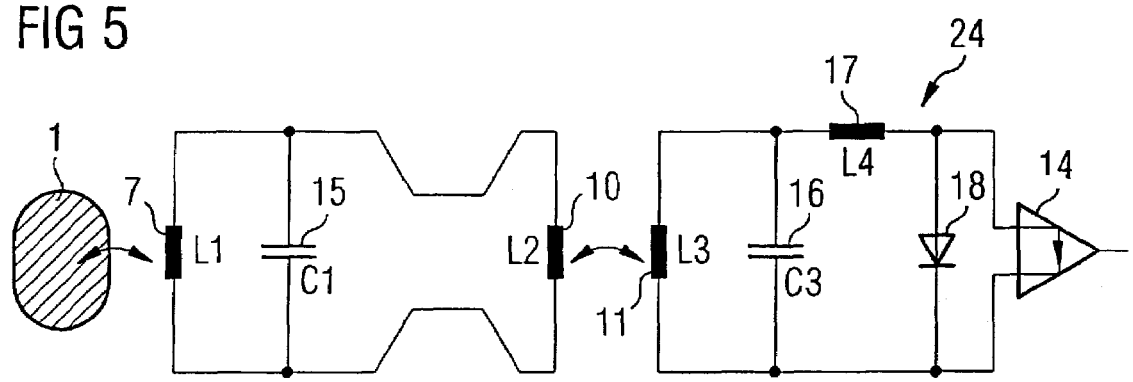
FIG. 5 schematically shows the signal flow from a local coil to an evaluation device.

According to FIG. 5, the attachment coupling element 10 and the base coupling element 11 are, for example, fashioned as inductive coupling elements 10, 11. The local coils 7 therefore exhibit an inductivity L1, the attachment coupling element 10 an inductivity L2 and the base coupling element 11 an inductivity L3. The local coil 7 is thereby tuned to the Larmor frequency of the magnetic resonance system by means of a capacitor 15 that exhibits a capacitance C1.

When the attachment coupling element 10 couples with one of the base coupling elements 11, the capacitor 15 and the attachment coupling element 10 form an oscillating circuit that is resonant at the Larmor frequency of the magnetic resonance system. The attachment coupling element 10 is therefore fashioned such that it detunes the local coil 7 when the local coil 7 cannot be coupled to the evaluation device 9. For protection against a possible malfunction of the attachment coupling element 10, it is thereby possible to install another safety element (for example a typical fuse) in the local coil 7 if necessary.

In an analogous manner, the base coupling element 11 should likewise be deactivated when it is not situated opposite an attachment coupling element 10. A controllable locking circuit 24 is therefore associated with the base coupling element 11. In the simplest case the locking circuit 24 comprises a capacitor 16, a coil 17 and a PIN diode 18. The capacitor 16 exhibits a capacitance C3, the coil 17 an inductance L4. If the PIN diode 18 is activated, the coil 17 and the capacitor 16 form a block circuit that is resonant at the Larmor frequency of the magnetic resonance system. The locking circuit 24 therefore separates the preamplifier 14 and the base coupling element 11 from one another. The base coupling element 11 is thus uncoupled from the preamplifier 14 at the Larmor frequency, thus can be detuned by means of the locking circuit 24.

When, in contrast to this, the base coupling element 11 couples with the attachment coupling element 10, transmission case and reception case must be differentiated.

In the transmission case the locking circuit 24 is activated. The base coupling element 11 therefore does not couple with the attachment coupling element 10, such that the attachment coupling element 10 furthermore detunes the local coil 7.

By contrast, in the reception case the locking circuit 24 is not activated, such that the local coil 7 is coupled to the preamplifier 14 via the attachment coupling element 10 and the base coupling element 11. The inductance L4 of the coil 16 is, however, selected such that in this case the local coil 7 is also only loaded in a high-ohmic manner.

Figure 6:
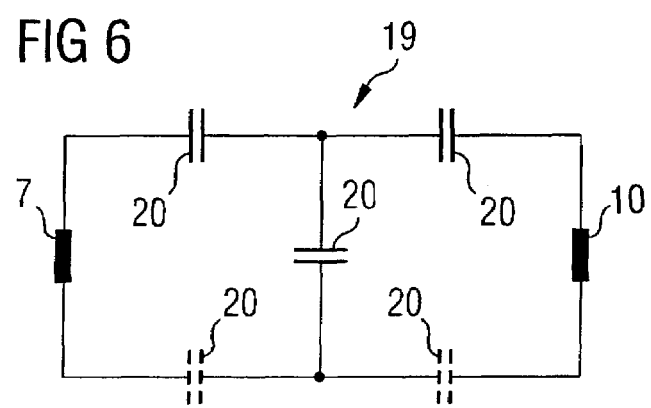
FIGS. 6 and 7 show a local coil and an attachment coupling element with a capacitive transformation circuit.
Figure 7:
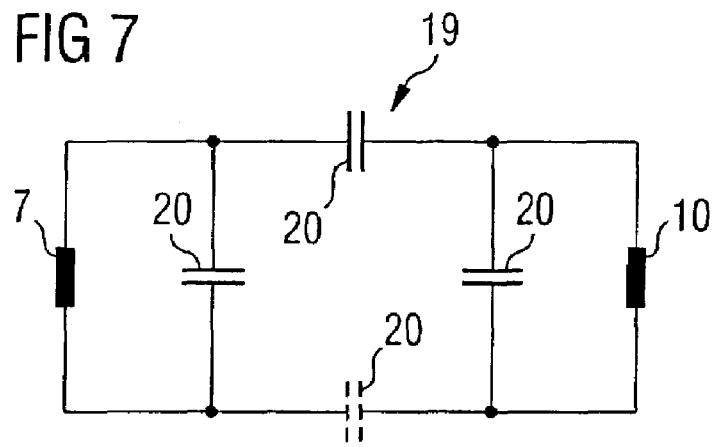

The unit from FIG. 5 (comprising local coil 7, capacitor 15 and attachment coupling element 10) is functional, however exhibits a relatively low SNR. According to FIGS. 6 and 7 a capacitive transformation circuit 19 that has a number of capacitors 20 is therefore arranged between the attachment coupling element 10 and the local coil 7. The capacitors 20 (drawn with solid lines in FIGS. 6 and 7) are necessary; the capacitors drawn with dashed lines are only optional. The impairment of the SNR can be limited to 1 to 2% with the embodiments according to FIGS. 6 and 7.

The attachment coupling element 10 should be designed such that it does not couple with the excitation field of the whole-body antenna (not shown).

In the example described above an inductive transfer is considered. Alternatively, the base volume element 11 and the attachment coupling element 10 can also be fashioned as capacitive coupling elements. This is schematically shown in FIG. 8.

Figure 8:
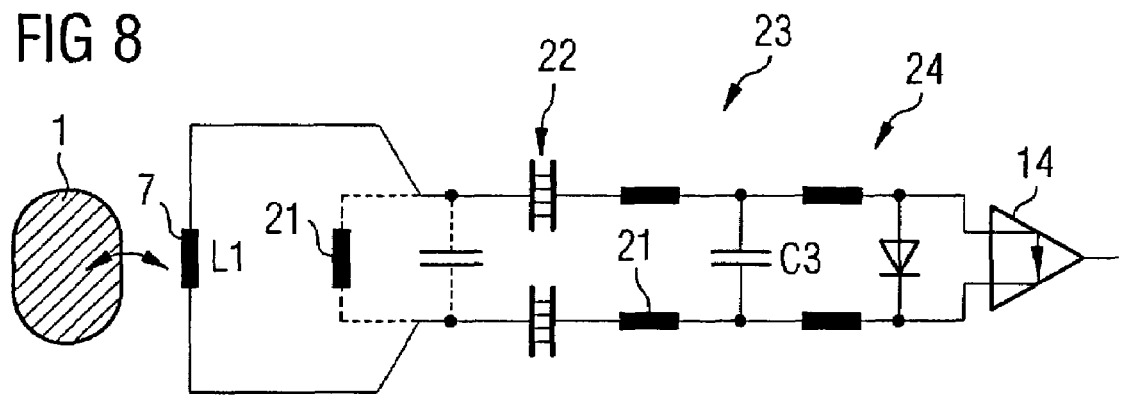
FIG. 8 schematically shows the signal flow from a local coil to an evaluation circuit.

In the embodiment in the form of capacitive coupling elements 22, according to FIG. 8 a protective circuit 23 is advantageously arranged between the base coupling element 11 and the evaluation circuit 9 (or, respectively, the preamplifier 14). According to FIG. 8, the protective circuit 23 comprises one or (as shown) two chokes 21 as well as a locking circuit 24. The locking circuit corresponds to the locking circuit from FIG. 5.

The protective circuit 23 has two functions. It compensates the series resistance of the local coil 7, the attachment coupling element 10, and the base coupling element 11 in the event that a magnetic resonance signal is fed to the evaluation device 9 from the local coil 7 via the attachment coupling element 10 and the base coupling element 11. It also detunes the base coupling element 11 in the event that no attachment coupling element 10 interacts with the base coupling element 11, such that the base coupling element 11 is not resonant at the Larmor frequency of the magnetic resonance system.

Furthermore, a choke 21 is connected in parallel with the attachment coupling element 10, such that the attachment coupling element 10 and the choke 21 form a radio-frequency block circuit at the Larmor frequency of the magnetic resonance system. Given capacitive coupling, the attachment coupling element 10 is thus also fashioned such that it detunes the local coil 7 when the local coil 7 cannot be coupled to the evaluation device 9.

The embodiments of the present invention described above concern the transfer of a magnetic resonance signal from the local coils 7 to the evaluation device 9. The local coils 7 are thus operated as reception coils. According to FIG. 9, however, it is also possible to operate the local coils 7 as transmission coils. This applies independently of whether the coupling elements 22 are fashioned as capacitive or inductive coupling element pairs 10, 11.

Figure 9:
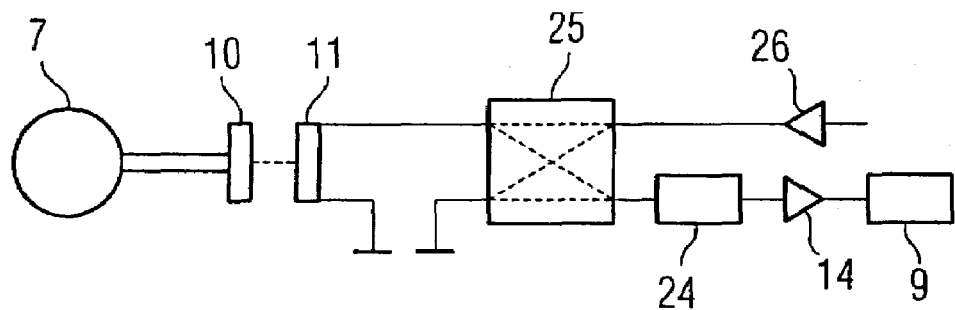
FIG. 9 illustrates an expansion of the inventive arrangement of transfer devices.

According to FIG. 9, a signal splitter 25 is arranged between the base coupling element 11 and the evaluation circuit 9. The signal splitter 25 is connected with an RF driver element 26. It is thus possible to feed a magnetic resonance excitation signal that is emitted from the RF driver element 26 into the local coil 7 via the base coupling element 11 and the attachment coupling element 10. This naturally applies only when the attachment part 6 is set on the base part 5 such that corresponding coupling elements 10, 11 couple with one another.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance system comprising:
   a magnet system that generates magnetic fields in an excitation region causing nuclei in an examination subject in the excitation region to be excited and emit a magnetic resonance signal;
   a reception antenna device comprising a plurality of local coils that receive the magnetic resonance signal, said local coils being disposed in proximity to the examination subject in the excitation region, said reception antenna device comprising a base part and an attachment part detachably placeable on the base part, configured to allow the examination subject to be located between the base part and the attachment part, when attached to each other;
   an evaluation device that evaluates respective magnetic resonance signals from the local coils;
   a base coupling element disposed at a predetermined base part location on the base part, and an attachment coupling element arranged at a predetermined attachment part location on the attachment part, said multiple local coils in the attachment part feeding their respective magnetic resonant signals to the evaluation circuit through the attachment coupling element and the base coupling element as long as the attachment part is placed on the base part; and
   a protective circuit connected between the base coupling element and the evaluation circuit, said protective circuit compensating for a series resistance of each local coil and the attachment element and the base coupling element that exists upon feed of a magnetic resonance signal from that local coil to the evaluation circuit, and said protective circuit detuning the base coupling element when no attachment coupling element is interacting with the base coupling element.

2. A magnetic resonance system as claimed in claim 1 comprising a pre-amplifier connected between said base coupling element and said evaluation device.

3. A magnetic resonance system as claimed in claim 1 wherein said base coupling element detunes at least one local coil at said at least one local coil cannot be coupled to the evaluation device.

4. A magnetic resonance system as claimed in claim 1 wherein each of said base coupling element and said attachment coupling element is an inductive transfer device.

5. A magnetic resonance system as claimed in claim 4 wherein each inductive transfer device comprises a capacitive transformation circuit comprising a plurality of capacitors connected between the base coupling element and a local coil.

6. A magnetic resonance system as claimed in claim 1 wherein said base coupling element and said attachment coupling element wherein each of said base coupling element and said attachment coupling element is a capacitive transfer device.

7. A magnetic resonance system as claimed in claim 6 wherein each capacitive transfer device comprises a pair of narrow coupling strips.

8. A magnetic resonance system as claimed in claim 7 wherein said coupling strips have longitudinal sides, and wherein the coupling strips are disposed adjacent to each other along their respective longitudinal sides.

9. A magnetic resonance system as claimed in claim 6 comprising a choke connected in parallel with the attachment coupling element.

10. A magnetic resonance system as claimed in claim 1 comprising a controllable locking circuit that detunes said base coupling element.

11. A magnetic resonance system as claimed in claim 1 comprising a signal splitter connected between the base part coupling element and the evaluation circuit, and an RF driver element connected to the signal splitter that emits a magnetic resonance excitation signal through the signal splitter to a local coil via the base coupling element and the attachment coupling element, as long as the attachment part is attached to the base part.

* * * * *